United States Patent [19]

Simon

[11] Patent Number: 5,479,945
[45] Date of Patent: Jan. 2, 1996

[54] METHOD AND A REMOVABLE DEVICE WHICH CAN BE USED FOR THE SELF-ADMINISTERED TREATMENT OF URINARY TRACT INFECTIONS OR OTHER DISORDERS

[75] Inventor: John G. Simon, Boston, Mass.

[73] Assignee: UroMed Corporation, Watertown, Mass.

[21] Appl. No.: 811,571

[22] Filed: Dec. 20, 1991

Related U.S. Application Data

[63] Continuation-in-part of Ser. No. 746,364, Aug. 16, 1991, abandoned, which is a continuation-in-part of Ser. No. 636,285, Dec. 31, 1990, Pat. No. 5,090,424.

[51] Int. Cl.⁶ ........................................... A61F 5/48
[52] U.S. Cl. ................... 128/885; 128/DIG. 25; 600/29
[58] Field of Search .................... 128/885, DIG. 25; 600/29–31

[56] References Cited

U.S. PATENT DOCUMENTS

| | | | |
|---|---|---|---|
| 3,789,828 | 2/1974 | Schulte | 600/30 |
| 3,797,478 | 3/1974 | Walsh | 600/29 |
| 4,019,499 | 4/1977 | Fitzgerald | 600/30 |
| 4,603,152 | 7/1986 | Laurin | 604/265 |
| 4,850,963 | 7/1989 | Sparks | 128/DIG. 25 |
| 4,938,759 | 7/1990 | Enscore | 600/29 |
| 4,946,449 | 8/1990 | Davis | 128/DIG. 25 |
| 4,981,465 | 1/1991 | Ballan | 128/DIG. 25 |
| 5,114,380 | 5/1992 | Larsen | 128/DIG. 25 |
| 5,114,398 | 5/1992 | Trick | 600/29 |
| 5,116,387 | 5/1992 | Burg | 600/30 |

FOREIGN PATENT DOCUMENTS

| | | |
|---|---|---|
| 0328421 | 8/1989 | European Pat. Off. . |
| 2431888 | 1/1976 | Germany . |

OTHER PUBLICATIONS

PCT Publication No. WO 9110466 Of Rochester Medical Corporation; Published Jul. 25, 1991.
PCT Publication No. WO 9004431 Of Chen, Fusen, H.: published May 3, 1990.

*Primary Examiner*—Michael A. Brown
*Attorney, Agent, or Firm*—Lorusso & Loud

[57] ABSTRACT

The present invention is a removable drug delivery system used by patients suffering from lower urinary tract infections or urine disorders and disorders of the urethra and bladder. The present invention delivers antibiotics to the infected areas utilizing modified urethral plugs. It is particularly advantageous in that it maintains a therapeutic effect without risking contamination. The device includes of a balloon at the proximal end and a fluid receiving port at the distal end. The balloon is inflated by injecting fluid into the fluid receiving port and deflated by pulling on a deflation string.

6 Claims, 8 Drawing Sheets

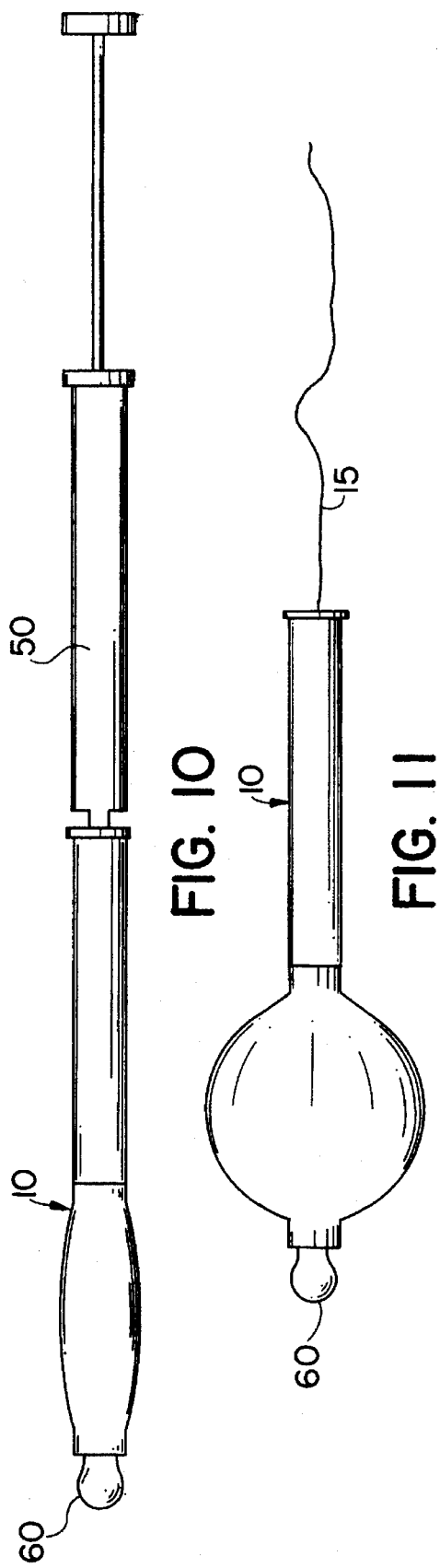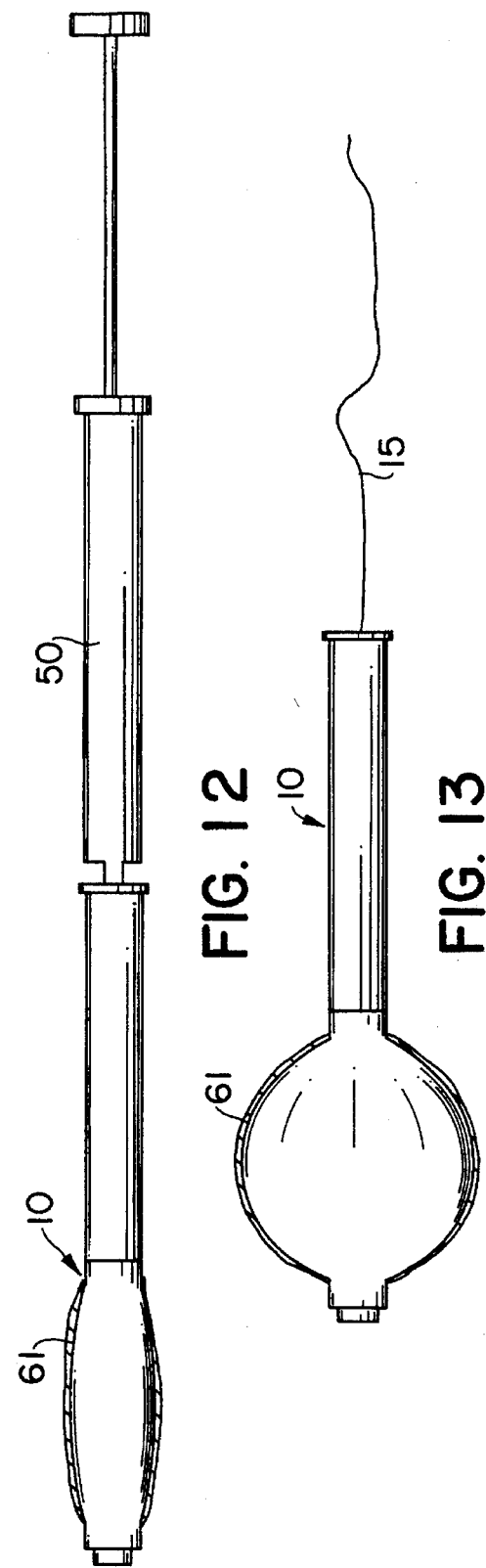

METHOD AND A REMOVABLE DEVICE WHICH CAN BE USED FOR THE SELF-ADMINISTERED TREATMENT OF URINARY TRACT INFECTIONS OR OTHER DISORDERS

CROSS REFERENCE TO RELATED APPLICATIONS

This application is a continuation-in-part of U.S. application Ser. No. 07/746,364 entitled "URETHRAL PLUG FOR THE TREATMENT OF INCONTINENCE" filed on Aug. 16, 1991, now abandoned which is a continuation-in-part of U.S. application Ser. No. 07/636,285 entitled "CONFORMABLE URETHRAL PLUG" filed on Dec. 31, 1990 now issued as U.S. Pat. No. 5,090,424 on Feb. 25, 1992. The teachings of the foregoing applications are incorporated herein by reference.

BACKGROUND OF THE INVENTION

1. Field of the Invention

The present invention is a novel urethral plug which can be used as a medicine delivery system by patients suffering from lower urinary tract infections or other urine disorders and disorders of the urethra and bladder.

The lower urinary tract is subject to a variety of bacterial illnesses and other disorders, which can be further characterized as renal, urethral, bladder, urethral and urinary. For example, bacteria infections of the lower urinary tract are very common, and after infancy occur about ten times more often in women than in men. The main route of infections in women ascends from the vagina through the urethra to the bladder. The majority of urinary tract infections (UTIs) are caused by gram negative bacteria such as Escherichia coli (up to 85% of UTIs), Klebsiella sp., Proteus sp., Enterobacter (Aerobacter) aerogenes, and Pseudomonas aeruginosa. Occasionally gram positive pathogens may be involved, including Staphylococcus epidermis (albus), and Staphylococcus aureus. The most common UTI is bacteriuria, or the proliferation of bacteria within the urine; as many as 10% of adolescent girls have this condition, often in asymptomatic form. The condition is considered deserving of treatment at bacterial counts above 100,000 per ml, and acute at counts above 500,000 per ml or more. Bacteriuria may lead to, or stem from, infections of the urethra and/or bladder. Most such conditions involve urea-splitting bacteria which render the urine alkaline and favor the formation of calcified deposits and urinary stones, which in turn harbor and protect the proliferating bacteria.

Infections involving bacteria in the urine and/or in the superficial regions of the urethral and bladder tissues should be highly amenable to treatment by the release of antibiotics into the urine in the bladder, or onto the walls of the urethra. The present invention comprises the delivery of antibiotics to the infected areas utilizing modified urethral plugs.

This invention is equally applicable to and intended for use in, other urine disorders and disorders of the bladder or urethra such as (e.g.) interstitial cystitis which can be treated chemically, by the action of a drug.

2. Prior Art

The principal therapy for UTIs involves antibiotics such as sulfonamides, tetracycline, ampicillin or amoxicillin, trimethoprim, trimethoprim/sulfamethoxazole, or ciprofloxacin hydrochloride. Oral doses typically on the order of a gram per day are usually maintained for 7–10 days, although 1–3 days is often effective. Recurrent infections are common and may be treated with additional medicines such as cephalosporins, nalidixic or oxolinic acid, or nitrofurantoin. Although this antibacterial therapy has markedly improved the prognosis for most UTIs, current methods of administering antibiotics have certain disadvantages which can be overcome by the present invention. Using oral means to deliver medicines for other disorders of course suffer from the same disadvantages.

Oral administration of antibiotics for the treatment of lower UTIs involves high doses, because the medicine must pass through the stomach, be absorbed by the intestines, survive first pass metabolism in the liver, accumulate in the blood, and finally accumulate in the urine and urinary tract in sufficiently high concentration to kill pathogenic organisms. This method is a very indirect means of administration, and leads to prolonged high systemic concentration of antibiotics. Under such conditions, many antibiotics have harmful side-effects such as ototoxicity and nephrotoxicity. The side effects limit the selection of antibiotics, and under the best of circumstances still expose the patient to small but undesirable risks.

Urinary medicines can also be administered by means of inserting conventional Foley catheters up the urethra to the bladder and instilling solutions via the Foley urine tube. Although this method delivers medication to where it is most needed, it is rarely used, and is almost never used unless the infection occurs in an already catheterized patient. Indwelling catheters tend to hinder free movement by the patient, and they preserve stagnant urethral conditions favorable to bacterial growth. Efforts to address the problems of indwelling catheters by repeated insertion and removal, introduces more bacteria into the infected urinary tract and may actually aggravates the infection. Moreover, existing catheters are expensive and not designed for easy self-administration. In addition, existing catheters have an open lumen for draining urine which also would drain out any antibiotic, limiting the effectiveness of any instillation.

SUMMARY OF THE INVENTION

The present invention is a removable medicine delivery system for use by patients suffering from lower urinary tract infections or other disorders of the urine, urethra and bladder. It is a removable delivery system which does not have an open lumen in connection with an external drainage bag. Hence the system of the present invention maintains therapeutic effect without risking contamination. The system comprises an improved urethral plug (delivery device), a solution of antibiotics or other therapeutic compound and soluble binder and a method of delivering the medicine to the infected or diseased urinary tract.

Infections involving bacteria or other disorders in the urine and/or in the superficial regions of the urethral and bladder tissues should be highly amenable to treatment by the direct release of antibiotics or other compounds into the urine in the bladder, or onto the walls of the urethra. The antibiotics or other compounds are adhered to the urethral plug or delivery device with the help of a soluble binder. The antibiotics or other compounds are dispersed in the soluble binder, and the solution is coated on the exterior surface of the delivery device. The solution can be coated onto the entire outer surface or on portions of the outer surface. Different types of antibiotics or other compounds can be coated onto different portions of the outer surface. Therefore, a variety of antibiotics or other compounds can be delivered to the infected or diseased areas. The delivery system is then inserted into the infected or diseased urethra or bladder.

The delivery device can be a simple plug. One preferred plug for use in the delivery system is the urethral plug disclosed in Simon et al, U.S. Ser. No. 07/746,364. Simon '364 is a urethral plug configured to fit within the urethra, bladder neck or bladder with a balloon at the proximal end, and a cap defining an aperture at the distal end. The urethral plug can easily be inserted and removed by the patient. The balloon is inflated by injecting fluid through the aperture at the distal end into the hollow plug whose lumen communicates with the interior of the balloon. Fluid may be injected through the plug by a syringe. After inflation, the balloon plugs the bladder neck and the urethra, and the antibiotics or other compounds then dissolve into the infected or diseased areas. The balloon is deflated by pulling on a deflation string projecting outwardly from inside the plug through the aperture on the cap. After the balloon is deflated, the plug may be removed.

Another important embodiment of an insertable urethral plug which may be employed to great advantage in the drug delivery system of the present invention is disclosed in Simon et al, U.S. Ser. No. 07/636,285. Simon '285 is a conformable urethral plug which has two components: a molded soft inflatable plastic catheter and a transportable fluid. After insertion, the fluid can be moved from an external bellows, through a check valve to inflate and distend the device within the urethra, bladder neck or bladder causing the device to plug the urethra and bladder neck. The antibiotics or other compounds dissolve into the infected or diseased areas. The device is deflated and removed by intentionally misaligning the check valve.

The medicine can also be delivered by means of a medicated pellet attached to the proximal end of urethral plugs. The antibiotic or other compound and binder solution can be covered by a permeable membrane to control the rate of discharge of antibiotics or other compounds to the infected or diseased areas. With this delivery system, the medicine can be delivered quickly and directly to the infected or diseased areas in high dosage. A further advantage is that the delivery can be halted immediately by removing the device.

Accordingly, an object of the present invention is to provide a removable medicine delivery system which treats urinary tract infections or other diseases.

Another object of the present invention is to provide a removable urethral plug which delivers the medicine to the infected or diseased urinary tract.

Another object of the present invention is to administer the medicine directly to the infected or diseased urinary tract.

Another object of the present invention is to provide a treatment for the infected or diseased urinary tract that requires less medicine than oral dosage.

Another object of the present invention is to provide a treatment for the infected or diseased urinary tract that results in lower systemic medicine levels and fewer side effects than oral dosage.

Another object of the present invention is to provide a greater freedom of choice of medicine in treating urinary tract infection or disease.

Another object of the present invention is to provide a medicine delivery system that can be easily used by the patients.

A further object of the present invention is to a provide fast acting method for the treatment of urinary tract infection or other disease.

Still a further object of the present invention is to provide a fast acting method for the treatment of urinary tract that can be easily and quickly halted.

Still another object of the present invention is to provide highly concentrated but brief pulses of antibiotics or other medication.

BRIEF DESCRIPTION OF THE DRAWINGS

FIG. 10 is a cross-sectional view of an embodiment of the drug delivery system of the present invention in a pre-insertion configuration showing a medicated pellet attached to the proximal end of the plug;

FIG. 11 is a cross-sectional view of the an embodiment of the drug delivery system of the present invention in an inflated and holding position showing a medicated pellet attached to the proximal end of the plug;

FIG. 12 is a cross-sectional view of an embodiment of the drug delivery system of the present invention in a pre-insertion configuration showing a medicated coating attached to the proximal balloon of the plug;

FIG. 13 is a cross-sectional view of an embodiment of the drug delivery system of the present invention in an inflated and holding position showing a medicated coating attached to the proximal balloon of the plug;

DESCRIPTION OF THE PREFERRED EMBODIMENT

At the outset, the invention is described in its broadest overall aspects with a more detailed description following.

The present invention is a medicine delivery system for the treatment of urinary tract infections (UTIs) or other disorders. The present invention utilizes a modified urethral plug as the delivery device, and a solution of antibiotics or other therapeutic compounds and soluble binder. The antibiotics or other therapeutic compounds are delivered directly to the infected or diseased area by the delivery device. The antibiotics or other therapeutic compounds are attached to the plug with the help of a soluble binder. A solution of antibiotics or other therapeutic compounds and binder is coated onto the outer surface of the delivery device. The coated delivery device is then inserted by the patient into the infected or diseased urinary tract. Inside the urinary tract, said solution dissolves into the urine or onto the wall of the urethra and thereby releases the antibiotics or other therapeutic compounds to treat the infection or disease.

The rate of discharge can be controlled by covering the coated solution of antibiotics and binder with a permeable membrane. The membrane slows down the rate of discharge by forcing the dissolving antibiotics or other therapeutic compounds to first pass through the membrane. Further, the membrane can also be selectively perforated to allow more control over the rate of discharge. The antibiotics or other compound can also be delivered by means of a medicated pellet attached to the proximal end of the urethral plug.

I. DELIVERY DEVICES

A. Simon et al U.S. Ser. No. 07/724,364

Simon '364 is a urethral plug comprising a balloon at its proximal end, a hollow main body which is in fluid communication with the balloon and with a fluid receiving port at the distal end of the main body. To deliver the antibiotics or other compound to the infected or diseased areas, the patient simply inserts the coated plug into the urethra and inflates the balloon. The balloon is inflated by injecting fluid into the hollow main body through the fluid receiving port. Fluid can be injected into the device with a syringe or other means. To remove the urethral plug the patient pulls on a string attached to the distal end of the device which deactivates a seal to deflate the balloon enabling the plug to be withdrawn.

Figure 1:
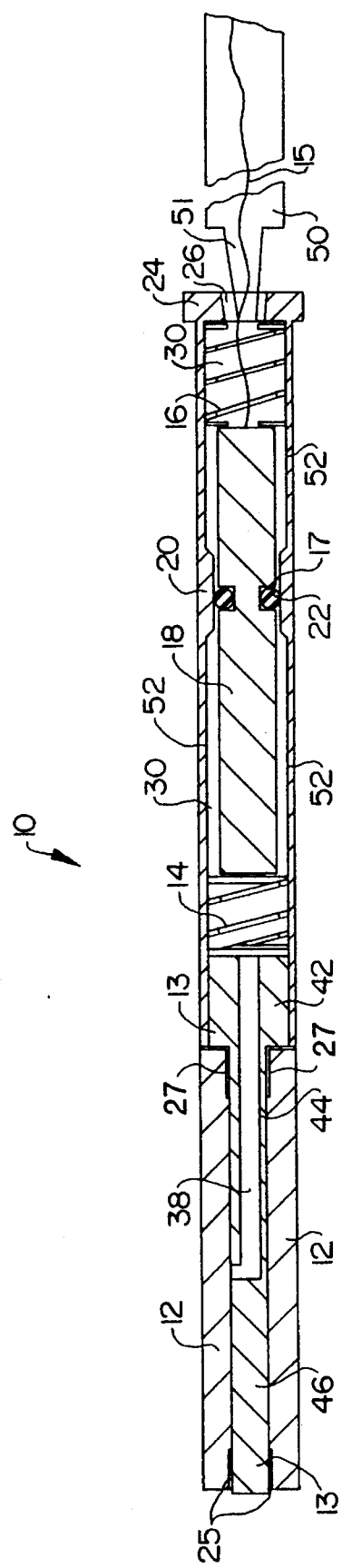
FIG. 1 is a cross-sectional view of the delivery device disclosed by Simon et al '364 in a pre-insertion configuration.

FIG. 1 is a cross-sectional view of a preferred embodiment of Simon '364 in its pre-insertion configuration. At the distal end, urethral plug 10 has distal cap 24. Distal cap 24 is used to anchor urethral plug 10 at the meatus urinarius or orifice of the urethra, preventing the migration of urethral catheter 10 into the bladder. Distal cap 24 defines aperture 26, which is located in the center of distal cap 24 and has a truncated cone shape with the larger opening facing outward. The fluid receiving port for the hollow main body of urethral plug 10 includes aperture 26 with which it is in fluid communication.

The main body of plug 10 is a fluid tight lumen for fluid to travel from the fluid receiving port to balloon 12, and comprises lumen 30 and balloon shaft 13. Lumen 30 is defined as the space between sheath 52 and plunger 18, which is located inside of sheath 52. Lumen 30 also includes the space within the two springs 14 and 16 affixed to each end of plunger 18. The springs 14 and 16 are used to keep plunger 18 in a predetermined static position. Force applied to plunger 18 can move it distally or proximally. When plunger 18 is moved, one spring is compressed, and the other is stretched storing energy in both springs. After the applied force is removed, the springs release the stored energy and return plunger 18 to its static position.

Balloon shaft 13 has a distal end and a proximal end and comprises three sections: hollow base section 42, hollow section 44 and solid section 46. Hollow base section 42 and hollow section 44 define tunnel 38. Balloon 12 is secured to balloon shaft 13 by means of affixing balloon 12 to glue joints 25 and 27. Only the ends of balloon 12 are affixed to glue joints 25 and 27 by means of epoxy adhesive. The middle part of balloon 12 is unattached and is free to expand or contract.

Figure 2:
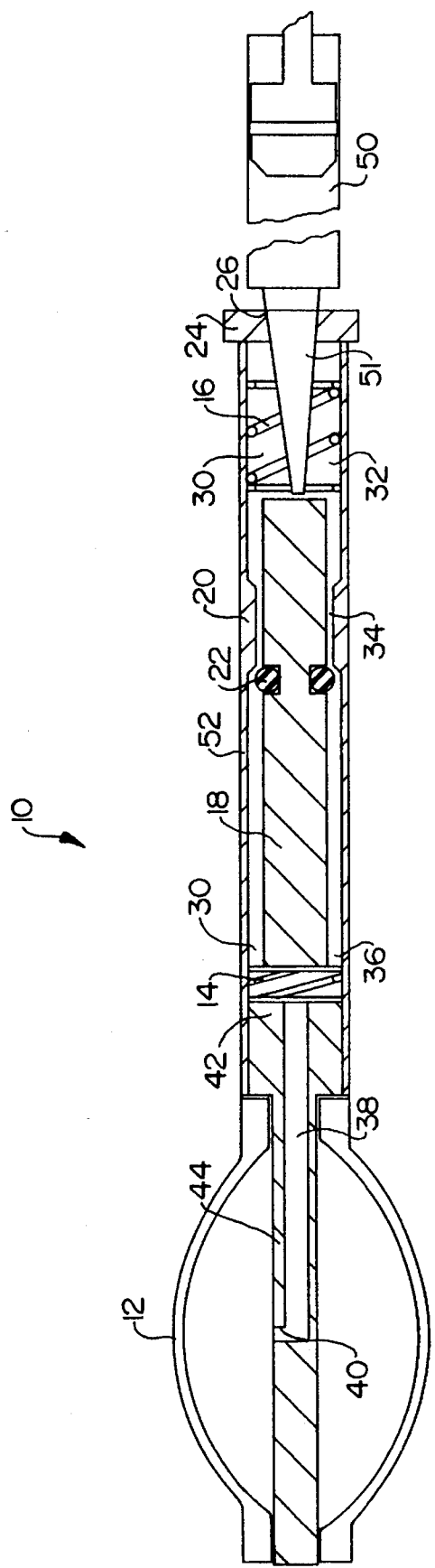
FIG. 2 is a cross-sectional view of the delivery device disclosed by Simon et al '364 in an inserted and inflated configuration.

Plunger 18 is a cylinder interrupted by groove 17, and has a proximal end and a distal end. Return spring 16 is affixed to distal cap 24 and to the distal end of plunger 18. Return spring 14 is affixed to the proximal end of plunger 18 and to the distal end of balloon shaft 13. O-ring 22 is secured to groove 17, and is large enough to protrude out of groove 17. In the static position groove 17 is aligned with internal ridge 20 forming passageway 34 which is shown in FIG. 2. In this position, O-ring 22 squashes against ridge 20 forming a seal, and seals off passageway 34. The seal keeps fluid from escaping when balloon 12 is inflated. Sheath 52 circumferentially covers urethral catheter 10 from base section 42 of balloon shaft 13 to return spring 16, inclusive. Sheath 52 abuts distal cap 24 and balloon 12. Ridge 20 is a part of sheath 52, and may be located approximately in the middle of sheath 52.

Now referring specifically to the fluid path, lumen 30 has three sections: distal lumen 32, passageway 34 and proximal lumen 36, as shown in FIG. 2. Distal lumen 32 is in communication with ambient via aperture 26, and is connected to passageway 34. Passageway 34 connects distal lumen 32 to proximal lumen 36. Distal lumen 32 and proximal lumen 36 are in fluid communication when passageway 34 is open. Passageway 34 is open when O-ring 22 is not aligned with ridge 20. O-ring 22 may be misaligned with ridge 22 by pushing plunger 18 proximally or pulling it distally until O-ring 22 is no longer in contact with ridge 20.

Lumen 36 is connected to tunnel 38. Tunnel 38 runs through the centers of base section 42 and hollow section 44, until it connects with nozzle 40 (FIG. 2). Nozzle 40 is orthogonal to tunnel 38. Fluid entering or exiting balloon 12 passes through nozzle 40.

Fluid may be injected by means of a syringe. Syringe 50 (FIG. 1) may be of any conventional design, but nose 51 should have a conical shape. During fluid injection, nose 51 should form a tight fluid seal with the conical shaped aperture 26 so that injected fluid can inflate balloon 12 and not leak outside. If the syringe does not form a seal with aperture 26, the fluid injected would spill back out through aperture 26 instead of filling up balloon 12, because spilling outward is the least resistance path for the fluid.

Figure 3:
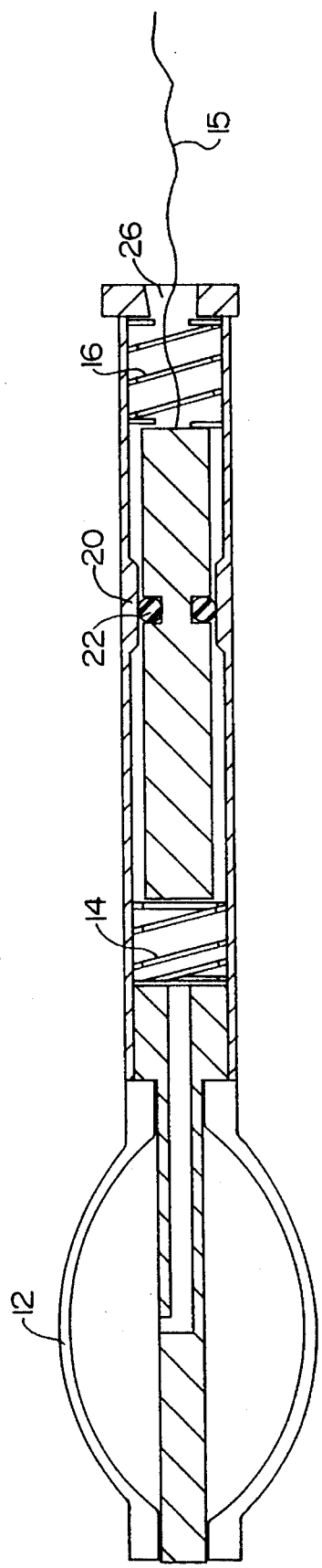
FIG. 3 is a cross-sectional view of the delivery device disclosed by Simon et al '364 in an inserted and holding configuration.

Now referring to the method for using urethral plug 10, a preferred embodiment as shown in FIG. 1 is inserted up the urethra until distal cap 24 abuts the orifice of the urethra. FIG. 2 shows urethral catheter 10 as it would be inserted in the urethra and in the process of inflation. Syringe 50 is introduced into aperture 26. Nose 51 pushed plunger 18 proximally, compressing return spring 14 and extending return spring 16. Energy is stored in both return springs 14 and 16. When O-ring 22 is pushed until it is no longer in contact with ridge 20, passageway 34 is open. Syringe 50 expels filling fluid into distal lumen 32. Filling fluid is then pushed through passageway 34 into proximal lumen 36, and into tunnel 38. Filling fluid then enters balloon 12 through nozzle 40. After balloon 12 is inflated, syringe 50 is withdrawn. Energy stored in return springs 14 and 16 is released, and pushes plunger 18 distally back to its static position. O-ring 22 is once again in contact with ridge 20, and seals off passageway 34 preventing filling fluid from escaping. Inflated balloon 12 plugs up the urethra, bladder neck or bladder. FIG. 3 shows urethral catheter 10 in its inflated holding position with deflation string 15 threading through aperture 26 and hanging outside of urethral catheter 10.

Figure 4:
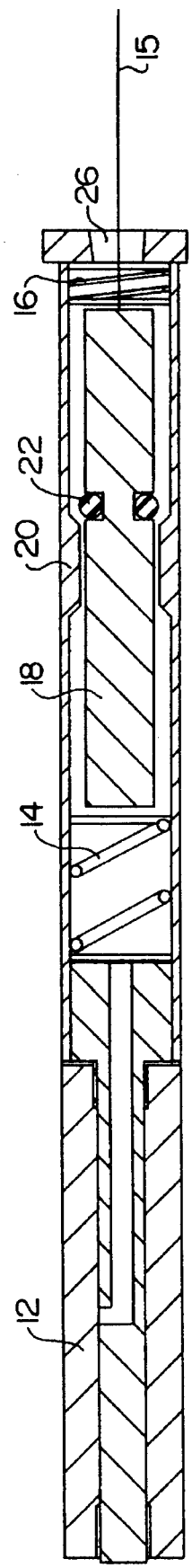
FIG. 4 is a cross-sectional view of the delivery device disclosed by Simon et al '364 in a deflated and removable configuration.

FIG. 4 describes the preferred embodiment in its deflated removable position. Filling fluid may be released by means of pulling on deflation string 15. When the patient wishes to deflate and remove urethral catheter 10 from the urethra, the patient simply pulls on string 15. Return spring 16 is compressed, and return spring 14 is extended. When O-ring 22 is no longer aligned with ridge 20, passageway 34 is open. Filling fluid is forced out through a path reversed from the path that it had entered, and balloon 12 deflates. After balloon 12 has been fully deflated, urethral catheter 10 may be removed. Urethral catheter 10 may be re-inserted and inflated as described above.

B. Simon et al, U.S. Ser. No. 07/636,285

The urethral plug disclosed in Simon '285 is a soft, flexible device which is inserted into the patient's urethra. It conforms to the shape and size of the urethra, especially upstream of the sphincter, toward the bladder neck. There is no need to custom make the device for each individual, although the device may be manufactured in several lengths and sizes. The patient's urethral length is measured by a physician to ensure that the proper size plug is used.

The plug has a hollow inner core with an increasing internal diameter toward the bladder neck. At the proximal end of the device there is an expandable sack, and at the distal end there is an inflatable bellows with a check valve. The check valve is located within a meatal plate, and said plate will anchor the plug at the meatus urinarius. The device is inserted into the urethra, so that the inflatable bellows is left outside the body, and the sack remains in the urethra, bladder neck or bladder.

The hollow inner core is filled with a fluid. When the device is inserted, the patient squeezes the inflatable balloon filled with the fluid, thus moving the fluid through the check valve into the sack at the proximal end. The inflated sack forms a plug by blocking the passage in the urethra, the bladder neck or the bladder itself. When the patient wishes to remove the plug, a gentle tug on the external part of the device will cause misalignment of the valve, and the fluid will move back down out of the sack into the balloon. Then, the device can be removed.

Figure 5:
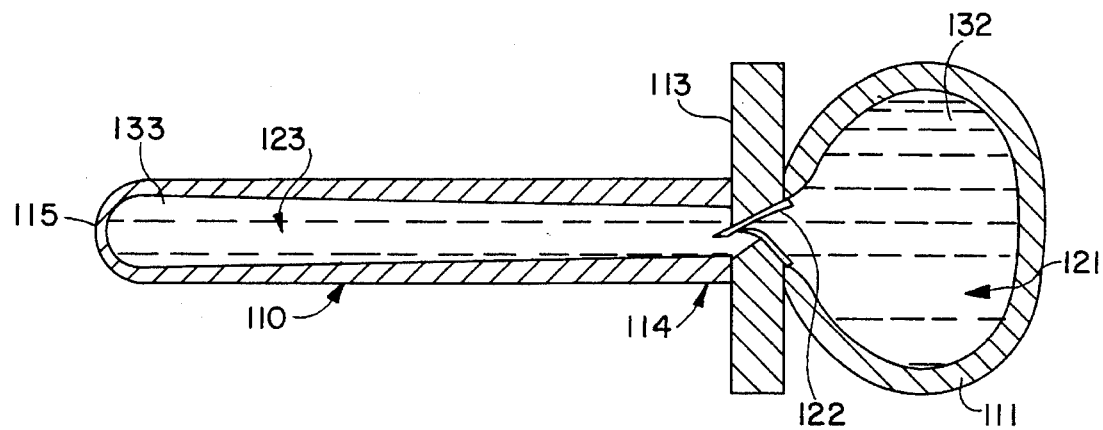
FIG. 5 is a cross-sectional view of the delivery device disclosed by Simon et al '285 in a deflated insertable configuration.

One embodiment of the device of the present invention is shown in FIG. 5 where a urethral plug 110 is shown. A bellows 111 defines cavity 121, and is used to transport fluid 132 contained in cavity 121 through a check valve 122 which is located within meatal plate 113. The bellows is made from a material which makes it conformable to the body and comfortable for the patient when the urethral plug is in place. The fluid 132 is transported to cavity 123 located within plug 110 becoming fluid 133. The wall of the plug is relatively constant in outer diameter allowing the device to be easily inserted. However, the wall thickness varies from the meatal plate 113, beginning at location 114 to the proximal end 115 where the wall is thinnest, allowing the greatest inflation. The fluid 132 can be any fluid which can be pumped from cavity 121 to cavity 123 through check valve 122.

Figure 6:
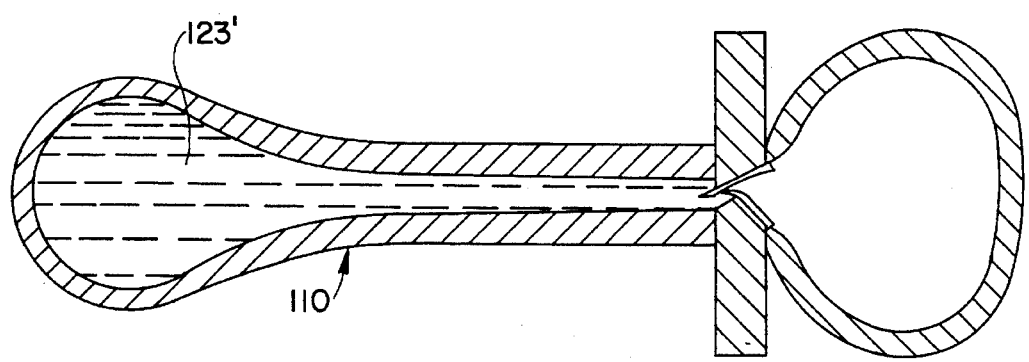
FIG. 6 is a cross-sectional view of the delivery device disclosed by Simon et al '285 in an inflated configuration.
Figure 7:
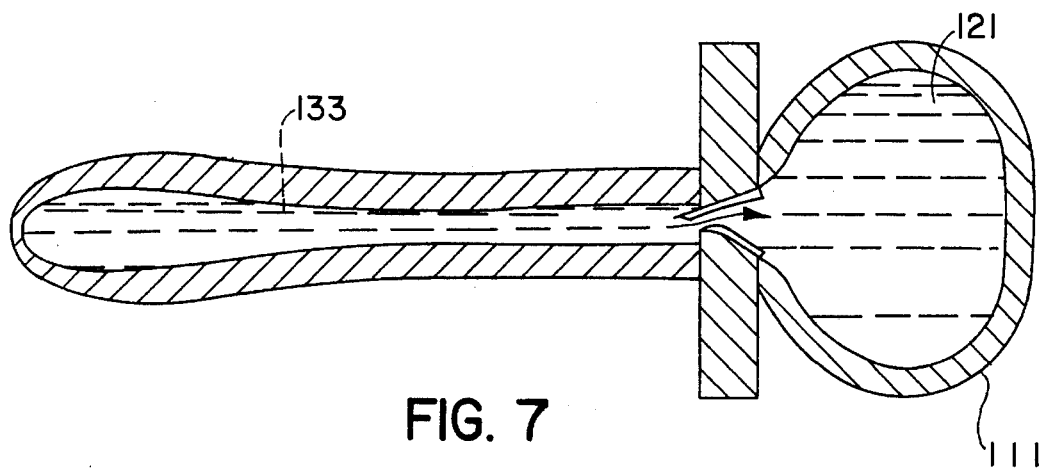
FIG. 7 is a diagrammatic representation of a method for deflating the delivery device disclosed by Simon et al '285.
Figure 8:
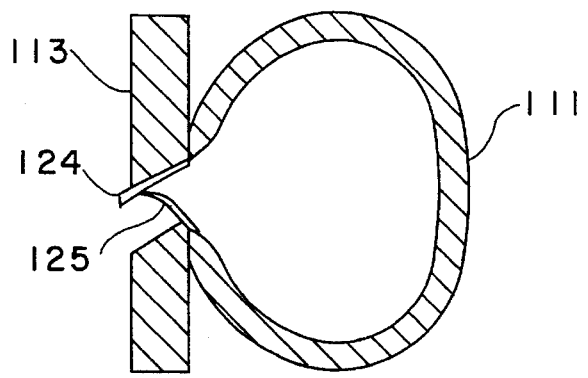
FIG. 8 is a cross-sectional view of the check valve of the delivery device disclosed by Simon et al '285 in a closed position.
Figure 9:
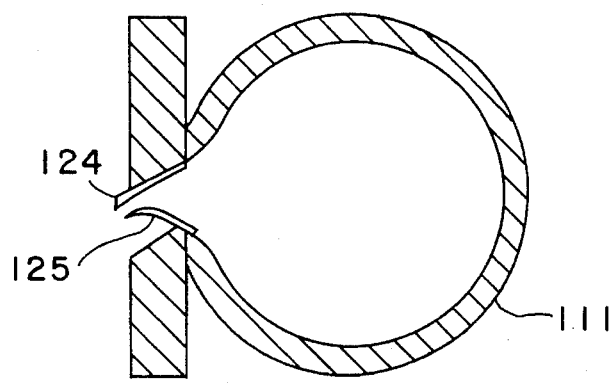
FIG. 9 is a cross-sectional view of the check valve of the delivery device disclosed by Simon et al '285 in an open position.

Check valve 122, shown in FIGS. 8 and 9, is designed to be asymmetric, functioning as a normal check valve. When bellows 111 is squeezed, fluid 132 is pumped from cavity 121 through valve 122. FIG. 6 shows cavity 123 inflated to a new configuration 123'. When it is desired to deflate cavity 123', the patient simply tugs on bellows 111 causing valve 122 to intentionally misalign, allowing fluid 133 to substantially return to cavity 121 such that there is pressure equilibrium between cavity 121 and cavity 123 as shown in FIG. 7.

FIG. 8 shows the intentional misalignment which is caused by leaf 124 being connected to meatal plate 113 such that it deflects minimally. On the other hand, leaf 125 is relatively flexible such that it moves in response to a patient-initiated tug on bellows 111, causing leaf 125 to separate from leaf 124. FIG. 9. shows leaf 125 separated from leaf 124. Thus, fluid may pass reversibly from cavity 123 back to cavity 121 through check valve 122 when bellows 111 is tugged upon.

II. ANTIBIOTIC OR OTHER COMPOUND COATING

It is difficult to coat antibiotic or other compounds directly onto the outer surface of the delivery device. However, if antibiotics are dissolved in solution with a binder such as polyvinylpyrrolidone, carboxymethylcellulose, gelatin, or a lactide-glycolide copolymer, the task can be accomplished. Following this step, the solution can be coated onto one or more portions of the outer surface of the delivery device. The solution can be coated on the shaft to treat infection or disease of the urethra, on the proximal distensible balloon to treat infection or disease in the bladder, on any portion of the balloon or on any combination thereof. Further, different solutions containing different types of antibiotics or compounds can be coated onto different portions of the surface of the delivery device.

The solution can also be coated onto the inside surface of a permeable elastic or heat-shrinkable silicone tubular membrane. The membrane is slipped over the shaft of the delivery device and warmed or allowed to contract in place trapping the solution of antibiotics and binder between the membrane and the delivery device.

Once inserted the antibiotics or other compound are dissolved into the urine in the bladder or released onto the wall of the urethra. The rate of dissolution can be controlled by means of the permeable membrane. The membrane reduces the rate of dissolution by forcing the antibiotics or other compound and binder to pass through the permeable membrane. The rate of dissolution can be controlled further by perforating the membrane to allow higher rate.

A similar tubular antibiotic or other compound-loaded membrane can then be applied over the extended proximal shaft of the delivery device, or alternatively the proximal tip of the device can be dip-coated with a dispersion of the antibiotics or other compounds and binder. Alternatively, a medicated pellet can be attached to the proximal end of the delivery device.

Figure 14:
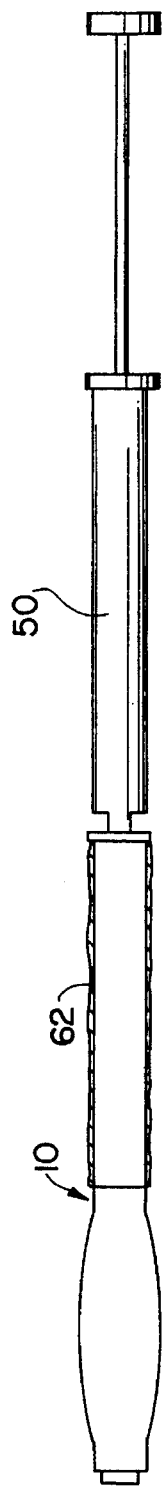
FIG. 14 is a cross-sectional view of an embodiment of the drug delivery system of the present invention in a pre-insertion configuration showing a medicated coating attached to the shaft of the plug.
Figure 15:
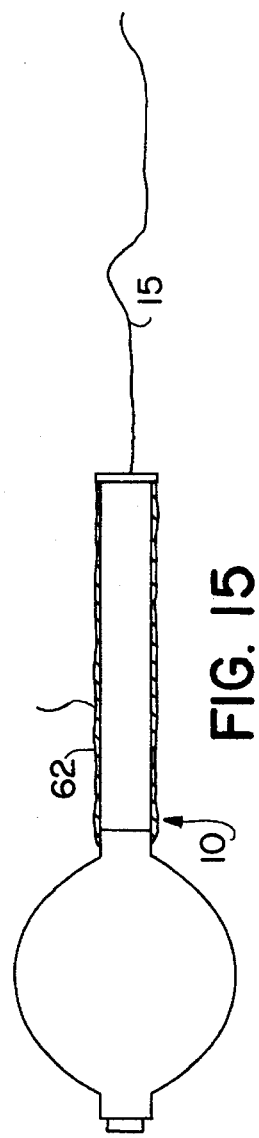
FIG. 15 is a cross-sectional view of an embodiment of the drug delivery system of the present invention in an inflated and holding position showing a medicated coating attached to the shaft of the plug.
Figure 16:
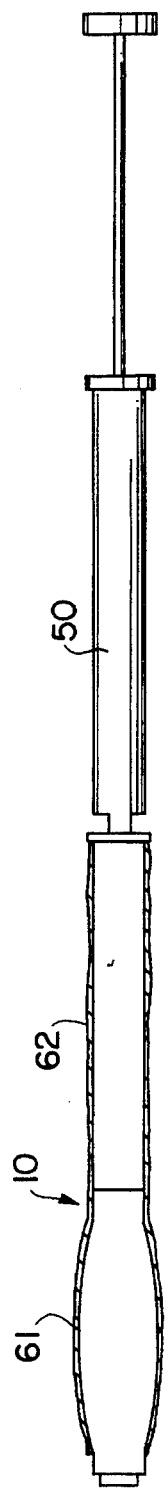
FIG. 16 is a cross-sectional view of an embodiment of the drug delivery system of the present invention in a pre-insertion configuration showing a medicated coating attached to the proximal balloon and the shaft of the plug.
Figure 17:
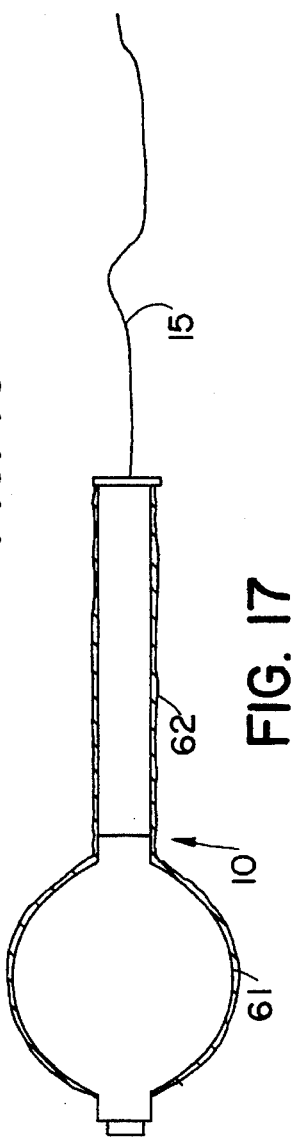
FIG. 17 is a cross-sectional view of an embodiment of the drug delivery system of the present invention in an inflated and holding position showing a medicated coating attached to the proximal balloon and the shaft of the plug.

FIGS. 10 and 11 show external insertion and holding views for a Simon '364 urethral plug improved by attaching an active medicated pellet 60 affixed to the proximal end of the delivery device, where it can dissolve into the urine. FIGS. 12 and 13 show the same end achieved by a medicated coating 61 over the outer the inflatable balloon. FIGS. 14 and 15 show similar views of a urethral plug modified by a medicated coating 62 on the wall of the shaft of the plug, where it can combat infection or other diseases in the walls of the urethra. FIGS. 16 and 17 illustrate that more than one outer surface can be utilized on a single delivery device. In any of these versions, an outer membrane may be useful for controlling and mediating the rate of dissolution of the solution of binder and antibiotics or other compound.

The invention is further illustrated by the following non-limiting example.

EXAMPLE

Antibiotic-loaded pellets are made by intimately mixing 300 mg of finely powdered ciprofloxacin hydrochloride with 1200 mg of finely powdered, high molecular weight polyvinylpyrrolidone (PVP), moistening the mixture with about 500 mg of acetone, and kneading with a spatula until a putty-like mass is obtained. From this material, kept in a closed container to avoid premature evaporation, a 200 mg portion is taken and pressed into a hemispherical mold 7.2 mm in diameter to produce a small hemisphere of similar dimension. Expelled from the mold and allowed to dry in a flow of dry air, the result is a hard, non-porous pellet about 6.6 mm in diameter and containing about 120 mg of PVP together with about 30 mg of entrained drug.

The flat surface of such a pellet is bonded to the flat end of a prototype urethral plug using cyanoacrylate glue. When immersed in an unstirred volume of 100 ml of simulated urine in a 250 ml beaker, the PVP pellet can be seen gradually to dissolve. After three hours a small residue remains on the end of the plug, while after four hours no remaining material can be seen either on the plug or within the surrounding liquid. Thus about 30 mg of ciprofloxacin has been delivered to the urine over a period of three to four hours.

For the treatment of urinary tract infections, ciprofloxacin is normally administered orally in 250 mg doses at 12 hour intervals. Its oral bioavailability is about 70%, and about 50% of the delivered drug is secreted in the urine. Thus about 175 mg of drug is excreted per day, or, on the average, about 30 mg in the course of a 4 hour period, essentially the same as the delivery rate provided by the pellet on the urethral plug. There is every reason to expect that insertion at four hour intervals of such a pellet mounted on a urethral plug would maintain a urine concentration of ciprofloxacin comparable with that produced by conventional oral administration, but with far less exposure of tissue to drug outside the bladder.

In other embodiments, modes of delivering antibiotics on a modified urethral plug include: diffusion of medicine solution stored in the annulus between two concentric balloons through the permeable walls of the outer balloon, effusion of medicine solution from a concentric balloon through a small orifice, and osmotic effusion through an orifice from a chamber behind a semipermeable membrane.

Thus, it is understood that the preceding description is given merely by way of illustration and not in limitation of the invention, and that various modifications may be made thereto without departing from the spirit of the invention as claimed. The scope of the invention should be construed in accordance with the accompanying claims, having due regard for changes that are obvious to those skilled in the art.

We claim:

1. A method for delivering antibiotics or other therapeutic compound to an infected or diseased urinary tract comprising the following steps:

providing a remove-to-void delivery device having an exterior surface having antibiotics or other therapeutic compound resident thereon, wherein said antibiotics or other therapeutic compound are resident on the delivery device through means of coating the exterior surface or portions of the exterior surface with a solution of, antibiotics or other compound and urine-soluble binder, prior to insertion, or by attaching a urine-soluble pellet containing antibiotics or other compound or both, prior to insertion, said remove-to-void delivery device further including an expandable proximal portion which can be inserted into the urethra, bladder or bladder neck, inserting the delivery device with the antibiotics or other therapeutic compound into the urethra, expanding the expandable portion of the device, allowing the antibiotics or other therapeutic compound to dissolve into the urine and/or onto the inner walls of the urinary tract, reversing the expansion of the expandable portion of the device, removing the device from the urethra.

2. The method as set forth in claim 1 wherein the antibiotics or other therapeutic compound are resident on the delivery device by means of coating the exterior surface or portions of the exterior surface with a solution of antibiotics or other therapeutic compound and urine-soluble binder.

3. The method as set forth in claim 1 wherein the antibiotics or other therapeutic compound are resident on the delivery device by means of attaching a urine-soluble pellet containing antibiotics or other therapeutic compound to the proximal end of the delivery device.

4. The method as set forth in claim 1 wherein the rate of dissolution into the urine is controlled by covering the solution of antibiotics or other compound and urine-soluble binder with a permeable membrane.

5. The method as set forth in claim 4 wherein the rate of dissolution of antibiotics or other compound into the urine is further controlled by perforating the permeable membrane.

6. A method of providing antibiotics or other therapeutic compound to an infected or diseased urinary tract comprising the following steps:

providing an expandable remove-to-void urethral plug having a means for expanding and a means for reversing the expansion, and an exterior surface free of orifices, said exterior surface having antibiotics or other therapeutic compound resident thereon, wherein said antibiotics or other therapeutic compound are resident on the delivery device through means of coating the exterior surface or portions of the exterior surface with a solution of, antibiotics or other compound and urine-soluble binder, prior to insertion, or by attaching a urine-soluble pellet containing antibiotics or other compound or both, prior to insertion, inserting said urethral plug into the urethra such that said coating dissolves from said exterior surface and disperses into the urinary tract, expanding said urethral plug with said means for expanding, so as to block the flow of urine, maintaining said urethral plug in the urethra for a period of time sufficient for said exterior surface to be substantially void of said coating, removing said urethral plug from the urethra for bladder evacuation by actuating said means for reversing the expansion, whereby said means for reversing the expansion is actuable without the aid of a device external to said plug.

* * * * *

UNITED STATES PATENT AND TRADEMARK OFFICE
CERTIFICATE OF CORRECTION

PATENT NO. : 5,479,945  
DATED : January 2, 1996  
INVENTOR(S) : Simon et al.

It is certified that error appears in the above-indentified patent and that said Letters Patent is hereby corrected as shown below:

ON THE TITLE PAGE AT NUMERAL [56],  
UNDER "References Cited U.S. PATENT DOCUMENTS", After "5,116,387  5/1992  Burg....................600/30"

insert --

```
    3,841,304    10/1974    Jones.....................128/1 R
    4,846,784     7/1989    Haber.......................600/29
    4,428,365     1/1984    Hakky.....................128/1 R
    2,638,093     5/1953    Kulick....................128-133
    3,646,929     3/1972    Bonnar....................128/1 R
    2,494,393     1/1950    Lamson......................128-1
    4,457,299     7/1984    Corewell..................128/1 R
    4,553,533    11/1985    Leighton..................128/1 R
    4,682,592     7/1987    Thoregard.................128/303
    5,024,658     6/1991    Kozlov.....................604/96
```

--; and

UNDER "OTHER PUBLICATIONS":

After "PCT Publication No. WO 9004431 Of Chen, Fusen, H.: published May 3, 1990."

UNITED STATES PATENT AND TRADEMARK OFFICE
CERTIFICATE OF CORRECTION

PATENT NO. : 5,479,945
DATED : January 2, 1996
INVENTOR(S) : Simon et al

It is certified that error appears in the above-indentified patent and that said Letters Patent is hereby corrected as shown below:

insert --

Nielsen et al., "The Urethra Plug: A New Treatment Modality for Genuine Urinary Stress Incontinence in Women", J. Urology, Vol. 44, p.1199 (1990).

--.

Signed and Sealed this

Twenty-second Day of October, 1996

Attest:

BRUCE LEHMAN

Attesting Officer

Commissioner of Patents and Trademarks